United States Patent [19]

Miyashita et al.

[11] 4,308,269
[45] Dec. 29, 1981

[54] MAYTANSINOIDS, PHARMACEUTICAL COMPOSITIONS THEREOF AND METHOD OF USE THEREOF

[75] Inventors: Osamu Miyashita, Osaka; Hiroshi Akimoto, Hyogo, both of Japan

[73] Assignee: Takeda Chemical Industries, Ltd., Osaka, Japan

[21] Appl. No.: 157,091

[22] Filed: Jun. 6, 1980

[30] Foreign Application Priority Data

Jun. 11, 1979 [JP] Japan ................................. 54-73789

[51] Int. Cl.³ ................. A61K 31/535; C07D 498/16; C07D 521/00
[52] U.S. Cl. .......................... 424/248.54; 260/239.3 P
[58] Field of Search .................................. 260/239.3 P; 424/248.54

[56] References Cited

U.S. PATENT DOCUMENTS 3,896,111 7/1975 Kupchan et al. ............. 260/239.3 T
4,137,230 1/1979 Hashimoto et al. ........... 260/239.3 P
4,162,940 7/1979 Higashide et al. ............ 260/239.3 P
4,225,494 9/1980 Higashide et al. ............ 260/239.3 P
4,248,870 2/1981 Miyashita et al. ............ 260/239.3 P

OTHER PUBLICATIONS

Kupchan et al., "Journal of Medicinal Chemistry" (1978) vol. 21, No. 1, pp. 31-37.
Journal of Pure and Applied Chemistry, vol. 11, Nos. 1 and 2 (1965) pp. 60, 61, 66-68 and 186-188.

Primary Examiner—Robert T. Bond
Attorney, Agent, or Firm—Wegner & Bretschneider

[57] ABSTRACT

Novel maytansinoids of the formula:

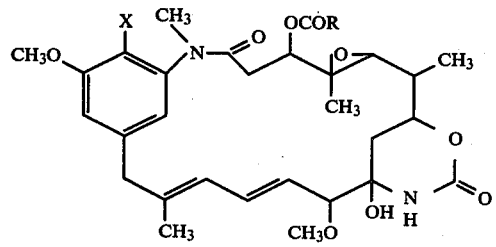

wherein X is H or Cl, and R is a hydrocarbon residue or an azaheterocyclic group, said R group having at least one of water-solubilizing substituents, have antimitotic, antitumor and antimicrobial activities.

11 Claims, No Drawings

MAYTANSINOIDS, PHARMACEUTICAL COMPOSITIONS THEREOF AND METHOD OF USE THEREOF

This invention relates to novel maytansinoid compounds of the formula:

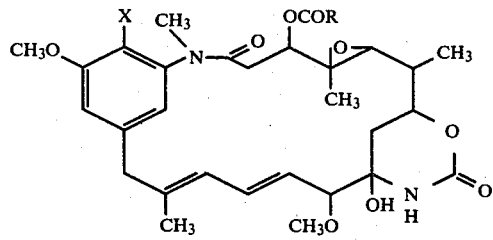

wherein X is H or Cl, and R is a hydrocarbon residue or an azaheterocyclic group, said R group having at least one of water-solubilizing substituents, and to their production and use.

Referring to the above formula (I), the hydrocarbon residue in R may be a hydrocarbon residue of 1-10 carbon atoms, for example, alkyl, aryl and aralkyl.

As examples of said alkyl, there may be mentioned $C_{1-8}$ alkyl (e.g. methyl, ethyl, propyl, isopropyl, butyl, isobutyl, sec-butyl, tert-butyl, pentyl, hexyl, heptyl, octyl). A preferred alkyl is $C_{1-4}$ alkyl.

Examples of said aryl include phenyl, and examples of said aralkyl include aryl-$C_{1-4}$ alkyl, especially phenyl-$C_{1-4}$ alkyl (e.g. benzyl, phenethyl, 1-phenylethyl).

The azaheterocyclic group in R may for example be 5- or 6-membered azaheterocyclic group containing one to four of N (e.g. pyidyl, pyrimidyl, pyrazinyl, pyridazinyl, triazinyl, piperidyl, piperazinyl, imidazoyl, pyrazolyl, triazolyl, tetrazolyl, pyrrolinyl, pyrazolinyl, imidazolinyl, pyrrolidinyl, pyrazolidinyl, imidazolidinyl, triazolidinyl).

The water-solubilizing substituent on the above hydrocarbon residue and azaheterocyclic group mean substituents to improve water solubility of the compound (I) and substituents which are capable of forming salts with acid or base to improve water solubility of the compound (I). As examples of said water-soluble substituents, there may be mentioned carboxyl, sulfo, amino, mono-substituted amino and quaternary ammonio groups. Examples of said mono-substituted amino group include $C_{1-4}$ alkylamino (e.g. methylamino, ethylamino, propylamino, isopropylamino, butylamino), $C_{3-4}$ alkenylamino (e.g. allylamino), benzylamino, arylamino (e.g. anilino), $C_{1-4}$ alkylsulfonylamino (e.g. methanesulfonylamino, ethanesulfonylamino), arylsulfonylamino (e.g. benzenesulfonylamino) and substituted arylsulfonylamino (e.g. p-toluenesulfonylamino).

Said quaternary ammonio groups may be represented, for example, by the formula:

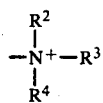

wherein each of $R^2$, $R^3$ and $R^4$ is independently $C_{1-4}$ alkyl, allyl or benzyl. Examples of said groups include trimethylammonio, triethylammonio, benzyldimethylammonio, allyldimethylammonio and dibutylmethylammonio groups.

The quaternary ammonio group may also be formed at the N atom on the ring of the above-mentioned azaheterocyclic group, and in that case, one or two of $R^2$, $R^3$ and $R^4$ may represent a bond or bonds. As examples of said azaheterocyclic group on which the quaternary ammonio group is formed, there may be mentioned pyridinio, pyrazinio, pyrimidinio, pyridazinio, imidazolio, pyrazolio, pyrrolinio, triazolio, tetrazolio, piperidinio, piperazinio, pyrrolidinio, pyrrolinio, imidazolinio, imidazolidinio, pyrazolinio and pyrazolidinio groups.

As concrete examples of these azaheterocyclic quaternary ammonio groups, there may be mentioned 1-pyridinio, 1-methyl-2-,3- or 4-pyridinio, 1-pyrazinio, 1,4-dimethyl-6-pyrazinio, 1,3-dimethyl-5-pyrimidinio, 1-methyl-3-pyridazinio, 1,1-dimethyl-3-piperidinio, 1,1-dimethyl-4-piperazinio, 1,4-dimethyl-4-imidazolio, 1,2,3-trimethyl-4-imidazolio, 1,3-dimethyl-2-pyrazolio, 1-methyl-3-(1,2,3-triazolio), 1-methyl-2-(1,2,5-triazolio), 1-methyl-3-(1,2,3,5-tetrazolio), 1-methyl-2-(1,2,4,5-tetrazolio), 1,2-dimethyl-5-triazolio, 1,3-dimethyl-4-triazolio, 1,3-dimethyl-5-tetrazolio and 1-methyl-2-(1,2,4,5-tetrazolio).

The above-mentioned quaternary ammonio group is accompanied with the corresponding anion such as halide ion (e.g. chloro-, bromo- or iodo- ion), hydroxide ion, nitrate ion, sulfate ion, perchlorate ion, phosphate ion, acetate ion, oxalate ion, fumarate ion, succinate ion, hydrogen fumarate ion, citrate ion, malonate ion, tartrate ion or hydrogen tartrate ion.

These azaheterocyclic groups having the quaternary ammonio groups may be combined with $C_{1-4}$ alkyl and may be present as quaternary ammonio heterocyclo(azanio)-$C_{1-4}$ alkyl groups.

Examples of said groups include 1-pyridiniomethyl, 1-methyl-2-,-3- or -4-pyridiniomethyl, 2-(1-methyl-3-pyridinio)ethyl, (1,3-dimethyl-4-imidazolio)methyl, 2-(1,3-dimethyl-4-imidazolio)ethyl, 1,2-dimethyl-4-(1,2,3-triazolio) methyl, 1,3-dimethyl-5-(1,2,3,4-tetrazolio)-methyl, 1,1-dimethyl-4-piperazino, 1-methyl-3-(1,2,3,5-tetrazolio)methyl and 1-methyl-2-(1,2,4,5-tetrazolio)-methyl.

The hydrocarbon residue and azaheterocyclic group may have, the same or different, plural number (e.g. two) of water-soluble substituents, and may also have other substituent(s) together with the water-soluble substituent(s). As examples of said substituents, there may be mentioned hydroxyl, $C_{1-4}$ alkoxy (e.g. methoxy, ethoxy, propoxy, isopropoxy, butoxy, isobutoxy), mercapto, $C_{1-4}$ alkylthio (e.g. methylthio, ethylthio, propylthio, isopropylthio) and halogen (e.g. chlorine, bromine, fluorine, iodine). When the hydrocarbon residue is alkyl, indolyl (e.g. 3-indolyl) may be added to the above substituents, and when R is aryl, aralkyl or azaheterocyclic group, $C_{1-4}$ alkyl (e.g. methyl, ethyl, propyl, isopropyl, butyl, isobutyl) may be added to the above substituents.

As concrete examples of R-groups, i.e. the hydrocarbon residues and azaheterocyclic groups having water-soluble substituents, there may be mentioned carboxymethyl, 2-carboxyethyl, 3-carboxypropyl, 4-carboxybutyl, 5-carboxypentyl, 6-carboxyhexyl, 7-carboxyheptyl, 8-carboxyoctyl, 2-methyl-3-carboxypropyl, 2,2-dimethyl-3-carboxypropyl, 1,3-dimethyl-3-carboxypropyl, 3,3-dimethyl-3-carboxypropyl, 4-carboxyphenyl, 2-carboxybenzyl, aminomethyl, 1-aminoethyl, 2-aminoethyl, 1-amino-1-carboxymethyl, 1-amino-2-carboxyethyl, 2-amino-2-carboxyethyl, 1-amino-3-carboxypropyl, 1-amino-4-carboxybutyl, 1-aminopropyl, 1-amino-2-methylpropyl, 1-amino-3-methylbutyl, 1-amino-2-methylbutyl, 1,5-diaminopentyl, 1-amino-2-methylthioethyl, 1-amino-2-methylsulfinylethyl, 1-amino-3-methylthiopropyl, 1-amino-3-ethylthiopropyl, 1-amino-2-phenylethyl, 1-amino-2-(p-hydroxy)phenylethyl, α-aminobenzyl, 1-amino-2-hydroxyethyl, 1-amino-2-hydroxypropyl, 1-amino-2-(3-indolyl)ethyl, 1-amino-2-(5-hydroxyindolyl-3)ethyl, 1-amino-2-(6-fluoroindolyl-3)ethyl, 1-amino-2-(4-chlorophenyl)ethyl, 1-amino-2-(4(5)-imidazolyl)ethyl, 2- or 3-aminopropyl, 4-aminobutyl, 2-diethylaminoethyl, 2- or 4-aminophenyl, 2-amino-4-chloropnenyl, 5-amino-2-chlorophenyl, 4-amino-2-hydroxyphenyl, 5-amino-2-hydroxyphenyl, 3,4- or 3,5-diaminophenyl, 2-hydroxy-5-pyridyl, 2-hydroxy-6-methyl-3-pyridyl, 2-carboxy-3-pyridyl, 2-carboxy-4-pyridyl, 2-carboxy-5-pyridyl, 2-carboxy-6-pyridyl, 4-carboxy-2-pyridyl, α-sulfobenzyl and 5-sulfo-2-hydroxyphenyl.

Among the above-mentioned compounds (I), a preferred embodiment provides compounds of the formula (I) wherein X is H or Cl, and R is $C_{1-8}$ alkyl, phenyl, phenyl-$C_{1-4}$ alkyl or 5- or 6-membered azaheterocyclic group containing one to four of N, said R group having one or two of water-soluble substituents selected from the group consisting of carboxyl, sulfo, quaternary ammonio group and amino which is unsubstituted or mono-substituted by $C_{1-4}$ alkyl, $C_{3-4}$ alkenyl, benzyl, phenyl, $C_{1-4}$ alkylsulfonyl, benzenesulfonyl of p-toluenesulfonyl.

The maytansinoid compound (I) of the present invention can be produced by acylating maytansinol or dechloromaytansinol of the formula:

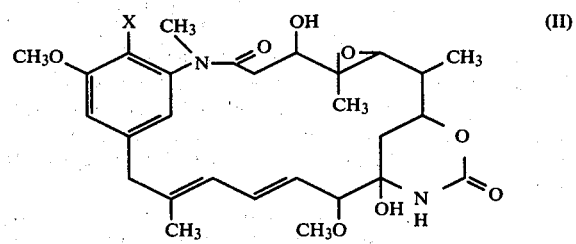
(II)

wherein X is as defined above, with a carboxylic acid of the formula:

wherein $R^1$ is a hydrocarbon residue or an azaheterocyclic group, said $R^1$ group having at least one of protected water-soluble substituents, or its reactive derivative with respect to the carboxyl function thereof, to obtain a compound of the formula:

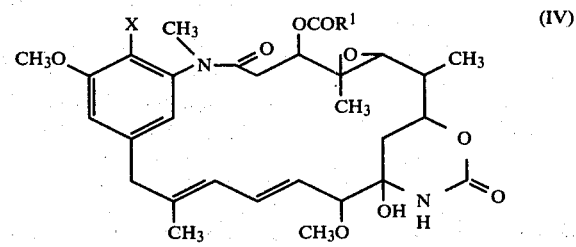
(IV)

wherein X and $R^1$ are as defined above, and by subjecting the obtained compound (IV) to a reaction for removal of the protecting group or a quaternizing reaction.

Referring to the above formula (III) and (IV), the hydrocarbon residue or azaheterocyclic group having at least one of the protected water-soluble substituents and being designated by $R^1$ represents a group which is convertible into R by subjecting the compound to a reaction for removal of the protecting group or a quaternizing reaction. More concretely, examples of said $R^1$-group include a group formed by protecting the water-soluble substituent (e.g. carboxyl, amino, mono-substituted amino) in the above-mentioned R-group with a protecting group known per se, or a group having a tertiary amino group in lieu of the quaternary ammonio group as the water-soluble substituent in the R-group.

As examples of the protecting groups for the water-soluble substituents such as carboxyl and amino, there may be mentioned known protecting groups for carboxyl and amino groups employed in the usual peptide syntheses. Said protected form of carboxyl may for example be an ester form of the formula —COOR$^5$ wherein R$^5$ is $C_{1-4}$ alkyl (e.g. methyl, ethyl, tert-butyl), methoxymethyl, phenyl, p-nitrophenyl, benzyl or p-methoxybenzyl. Said protecting groups for amino and mono-substituted amino group may for example be formyl, acetyl, halogenated acetyl (e.g. chloroacetyl, trichloroacetyl, trifluoroacetyl), benzyloxycarbonyl and tert-butoxycarbonyl.

As protected forms of sulfo group, there may be mentioned its alkali metal salts (e.g. sodium salt, potassium salt) and its esters with $C_{1-4}$ alkanol (e.g. methanol, ethanol, propanol, isopropanol, butanol, isobutanol), cyclopentanol or cyclohexanol.

An exemplary reaction procedure comprises acylating a compound (II) with a carboxylic acid (III) in the presence of a carbodiimide. Based on compound (II), carboxylic acid (III) may be used in an amount of, for example, about 1 to 50 molar equivalents and, in many cases, is preferably employed in an amount of about 1–20 molar equivalents. The carbodiimide may be used in an amount of about 1 to 70 molar equivalents based on compound (II) and, in many cases, is preferably employed in an amount of about 1–30 molar equivalents. The usable carbodiimide is preferably dicyclohexylcarbodiimide, although such other carbodiimides may also be employed as, for example, diphenylcarbodiimide, di-o-tolylcarbodiimide, di-p-tolylcarbodiimide, di-tert-butyl-carbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide and 1-ethyl-3-(3-dimethylaminopropyl)carbodiimide.

This acylation reaction may be carried out in a suitable solvent. Examples of such solvent include esters (e.g. ethyl acetate), ethers (e.g. diethyl ether, dioxane, tetrahydrofuran), halogenated hydrocarbons (e.g. methylene chloride, chloroform), nitriles (e.g. acetonitrile), aromatic hydrocarbons (e.g. benzene), nitromethane, pyridine, dimethylformamide, dimethylsulfoxide, sulfolane, etc., as well as appropriate mixtures of such solvents.

This reaction may be usually carried out at a suitable temperature from ice-cooling to the reflux point of the reaction system.

This acylation reaction can be advantageously hastened with the aid of a catalyst capable of promoting acylation of compound (II). The catalyst may be an appropriate acid or base. The basic catalyst includes, among others, tertiary amine compounds (e.g. aliphatic tertiary amines such as triethylamine; aromatic tertiary amines such as pyridine, α-, β-, or γ-picoline, 2,6-lutidine, 4-dimethylaminopyridine, 4-(1-pyrrolidinyl)pyridine, dimethylaniline, diethylaniline), halogenated alkali metals (e.g. potassium fluoride, anhydrous lithium iodide), salts of organic acids (e.g. sodium acetate) and so forth. The acid catalyst includes, among others, Lewis acids (e.g. anhydrous zinc chloride, anhydrous aluminum chloride (AlCl$_3$), anhydrous ferric chloride, titanium tetrachloride (TiCl$_4$), stannic tertrachloride (SnCl$_4$), antimony pentachloride, cobalt chloride, cupric chloride, boron trifluoride etherate, etc.), inorganic strong acids (e.g. sulfuric acid, perchloric acid, hydrochloric acid, hydrobromic acid, etc.), organic strong acids (e.g. benzenesulfonic acid, p-toluenesulfonic acid, trifluoroacetic acid, trichloroacetic acid, etc.), acidic ion exchange resins (e.g. polystyrenesulfonic acid), etc. The catalyst is used in a catalytic amount sufficient to promote acylation, for example, about 0.01 to about 10 molar equivalents, preferably about 0.01 to about 1 equivalent, based on carboxylic acid (III). The use of such a catalyst leads in many cases to remarkably improved yields of compound (IV).

In connection with this reaction, if the carboxylic acid (III) is isomeric, i.e. D- and L-isomers, such isomers may be employed either independently or as an optional mixture. When compound (I) having an optically active acyl group is desired, the use of the corresponding optical form of carboxylic acid (III) proves advantageous in some instances. There also are cases in which even the use of an optically active carboxylic acid (III) gives rise to a mixture of D- and L-isomers of maytansinoid compound (I).

The acylation process utilizing a reactive derivative of carboxylic acid (III) with respect to its carboxyl function may for example be a process which comprises using a derivative having a functional group capable of acylating the 3-position of compound (II) such as the acid anhydride (and mixed acid anhydride cyclized through α-OH and carbonic acid) of carboxylic acid (III). The solvent and catalyst for use in this acylation reaction may be the same as those mentioned hereinbefore in connection with acylation in the presence of a carbodiimide. The reaction temperature may usually range from about −20° C. to about +100° C. and preferably about 20° C. to about 40° C. The reaction may be hastened by heating the reaction system to a still higher temperature.

The compound (IV) thus produced may be isolated by a conventional procedure or may not be isolated, and then may be subjected to a reaction for removal of the protecting group or a quaternizing reaction to obtain the contempleted compound (I).

Examples of the reaction for removal of the protecting group includes hydrolysis by means of an acid or a base, other decomposition by means of an acid or a base (e.g. amine) than hydrolysis, and catalytic reduction. More concretely, when carboxyl or sulfo group is protected in the form of methyl ester, ethyl ester or phenyl ester, the protecting group may be removed by treating it with an aqueous solution of alkali hydroxide or an amine, and when protected in the form of methoxymethyl ester, p-methoxybenzyl ester or t-butyl ester, the protecting group may be removed by hydrogen chloride or hydrochloric acid. Acetyl, trichloroacetyl or trifluoroacetyl group as the protecting group for the amino group may be removed by treating with an aqueous alkaline solution, and chloroacetyl group may be removed by treating with phenylenediamine, ethylenediamine or thiourea, and t-butoxycarbonyl group may be removed by treating with an acid such as trifluoroacetic acid. Five or six membered cycloalkyl as the protecting group for sulfo group may be removed by heating to a temperature from room temperature (18°–28° C.) to about 50° C.

The quaternization may be carried out by reacting the compound (IV) having a tertiary amino group including a tertiary N atom in the azaheterocyclic group, with an alkylating agent such as an alkyl or aralkyl halide (e.g. methyl iodide, methyl bromide, ethyl iodide, ethyl bromide, benzyl bromide), a dialkyl sulfate (e.g. dimethyl sulfate, diethyl sulfate) or an oxonium salt (e.g. trimethyloxonium fluoroborate, triethyloxonium fluoroborate). Said alkylating agent may be used generally in an amount of 1–50 molar equivalents and preferably 1–10 molar equivalents based on the tertiary amino group. The reaction may be carried out in the absence or presence of an inert solvent (e.g. water, methanol, ethanol, dichloromethane, chloroform, tetrahydrofuran, dioxane, acetone, acetonitrile) and at a suitable temperature from ice-cooling to the refluxing temperature of the reaction solvent.

The maytansinoid compound (I) thus produced by the above-mentioned acylation can be isolated by subjecting the reaction mixture to a conventional procedure such as concentration, solvent extraction, chromatography, recrystallization, etc. When maytansinoid compound (I) is produced as a mixture of isomers (e.g. D- and L-isomers), the isomers can be separated from each other generally by a conventional procedure, e.g. silica gel column chromatography. The compound (I) may be isolated as a salt. As examples of said salt, when the water-soluble substituent of compound (I) is carboxyl or sulfo, there may be mentioned alkali metal salts (e.g. sodium salt, potassium salt), and when the water-soluble substituent is, amino or mono-substituted amino, there may be mentioned acid addition salts with inorganic acids (e.g. hydrochloric acid, hydrobromic acid, hydroiodic acid, sulfuric acid, nitric acid, phosphoric acid, perchloric acid, tetrafluoro boric acid or organic acids (e.g. acetic acid, lactic acid, oxalic acid, succinic acid, fumaric acid, maleic acid, tartaric acid, malonic acid, p-toluenesulfonic acid, trifluoroacetic acid, picric acid). The maytansinoid compound (I) according to this invention includes such individual isomers, all mixtures of the isomers and salts.

The maytansinoid compound (I) according to this invention has strong antimitotic and antitumor activities with comparatively low toxicity and improved water-solubility, and are therefore suited for administration, oral or parenterally, to tumor-bearing warm-blooded animals (e.g. mouse, rat, rabbit, dog, cat and man) for the purpose of prolonging their survival times. Each compound (I) is normally administered in the form of a pharmaceutical preparation (e.g. injectable solution) as formulated with a carrier, diluent or the like which is known per se.

When compound (I) is administered in the form of an injectable preparation, it may be given subcutaneously, intraperitoneally, intravenously or intramuscularly, for instance. The dosage of compound (I) varies with the kind, sympton, administration route, etc. but, for example, in case of intravenous administration for prolonging life span of the animal suffering from leukemia or melanoma, it may be decided from the range of about 1 to 1000 μg/kg body weight, preferably about 10 to 500 μg/kg body weight, especially about 20 to 250 μg/kg body weight, per dose.

The injectable preparation can be prepared by the established pharmaceutical procedure; for example by dissolving about 50 μg to 3 mg of compound (I) in each about 0.5 ml of alcohol (e.g. ethanol), followed by addition of a sufficient amount of physiological saline to make a total of 10 ml. When a small dosage is indicated, the above solution may be further diluted with physiological saline.

The maytansinoid compounds (I) according to this invention are of value also in that they have antimicrobial activity, e.g. antifungal and antiprotozoal properties. Thus, for example, the maytansinoid compounds (I) are useful for treating *tetrahymena pyriformis W*. As an antifungal or antiprotozoal agent, compound (I) is instrumental in assays of the bacterial flora of soil, active sludge, animal body fluids, etc. Thus, for the isolation of useful bacteria from soil samples or in the assay of activity of bacteria to the exclusion of those of protozoa and fungi in connection with the operation and analysis of active sludge systems for waste water treatment, the compound (I) can be advantageously employed to ensure selective growth of bacteria without permitting growth of the concomitant protozoa and fungi. Thus, such a sample is added to a liquid or solid medium, and per milliliter of the inoculated medium, 0.1 ml of a 1% methanol-water solution of about 10 to 100 μg/ml of compound (I) is added, and then incubated to let the bacteria grow and multiply.

The maytansinoid compound (I), in an amount of 0.02 ml of a 1 mg/ml aqueous solution, is able to inhibit growth of causative microorganisms of stem rot, helminthosporium leaf rot and sheath blight in rice plants, for instance, and can therefore be used for the treatment of such plant diseases. The procedure may comprise dissolving compound (I) in 1% aqueous methanol to a concentration of about 0.5 to 5 μg/ml and spraying rice plants with the solution.

The above-mentioned compound (IV) also has the same antimitotic, antitumor, antifungal and antiprotozoal activities as those of the present compound (I), and it may be usable in the same ways and procedures as those of the compound (I).

The following reference examples and working examples are intended to describe this invention in further detail and not to limit its scope. In these examples, Rf values are determined by the thin layer chromatography on a precoated silica-gel plate (Merck, HPTLC).

REFERENCE EXAMPLE 1

In 800 ml of dry tetrahydrofuran (THF) is dissolved 15.0 g of antibiotic Ansamitocin mixture (12% of ansamitocin P-2, 71% of P-3 and 17% of P-4) and under dry nitrogen gas streams, the solution is cooled to −50° C. in a dry ice-acetone bath. Then, 13.0 g of lithium aluminum hydride (LAH) is added in a single dose and the mixture is stirred at −50° C. to −22° C. for 2 hours. Then, at −28° C., a further 3 g of LAH is added and the reaction mixture is stirred at −28° C. to −22° C. for 80 minutes. Thereafter, at −50° C., 750 ml of 2N HCl is added dropwise with caution and the reaction mixture is extracted three times with 2.6 l, 1.6 l and 0.8 l portions of ethyl acetate. The extracts are pooled, washed with a saturated aqueous solution of sodium chloride (100 ml×2) and dried (MgSO$_4$, 250 g). The solvent is distilled off under reduced pressure and the residue (13.6 g) is chromatographed on a column of silica gel (1.2 kg), elution being carried out with ethyl acetate-water (98.5:1.5, V/V). The eluate is collected in 400-gram fractions. Fractions 35 through 52 are pooled, the solvent distilled off and the residue dried in vacuo to obtain 7.25 g of maytansinol. Then, fractions 53 through 68 are similarly treated to obtain 1.55 g of a substantially equimolar mixture of maytansinol and dechloromaytansinol. Similarly, fractions 69 through 86 yield 0.78 g of dechloromaytansinol.

This product is reprecipitated from chloroform-hexane to obtain 0.71 g of dechloromaytansinol. m.p. 174°–179° C. (decompn.)

Mass spectrum (m/e): 469, etc.

UV spectrum ($\lambda_{max}^{MeOH}$) nm: 231.5, 241.5, 250.5, 277.5, 286

REFERENCE EXAMPLE 2

Maytansinol 3-isonicotinate

Maytansinol (98.4 mg, 0.174 mmol), isonicotinic acid (131.5 mg, 1.07 mmols), dicyclohexylcarbodiimide (DCC) (252.3 mg, 1.22 mmols) and 4-dimethylaminopyridine (DMAP) (43.4 mg, 0.356 mmol) are reacted in 10 ml of dry dichloromethane at room temperature for 2 hours. The reaction mixture is then concentrated under reduced pressure, a small amount of ethyl acetate added to the residue, the insolubles filtered off, and the filtrate concentrated to dryness. The residue is chromatographed on silica gel (75 g) and elution is carried out with H$_2$O-saturated ethyl acetate (ca 2 l), the eluate being collected in 16-g fractions. Fractions 34 through 70 are pooled, the solvent distilled off and the residual crude product dissolved in a small amount of ethyl acetate. The solution is allowed to stand and the resultant crystals are recovered by filtration. By the above procedure is obtained 28.0 mg of maytansinol 3-isonicotinate as white crystals melting at 185°–187° C. (decompn.)

UV spectrum ($\lambda_{max}^{MeOH}$) nm: 233, 240(sh), 252.2, 281, 289

Mass spectrum (m/e): 608, 593, 576, 573, 566, 502

REFERENCE EXAMPLE 3

In 30 ml of dry dichloromethane are dissolved 310 mg of maytansinol, 582 mg of N-tert-butoxycarbonyl-N-methyl-L-alanine and 549 mg of DCC. The solution is stirred at room temperature for 15 minutes, after which 207 mg of DMAP is added. The mixture is stirred at room temperature overnight, the precipitate is filtered off and the filtrate is diluted with ethyl acetate to a volume of 150 ml. This diluted solution is washed with a mixture of 50 ml of water and 2 ml in a 1N-HCl, water (50 ml) and an aqueous solution of sodium hydrogen carbonate (50 ml) in the order mentioned. The organic layer is taken, dried over Na$_2$SO$_4$, and evaporated. The residue is dissolved in chloroform and subjected to silica gel (100 g) column chromatography (solvents: chloroform and, then, chloroform-methanol=50:1 v/v) to give 11 mg of maytansinol 3-(S)-α-(N-methyl-N-tert-butoxycarbonyl) aminopropionate and 61 mg of maytansinol 3-(R)-α-(N-methyl-N-tert-butoxycarbonyl)aminopropionate. The (S) compound:

Mass spectrum (m/e): 750, 688, 632, 588, 573, 486, 485, 450, etc.

UV spectrum ($\lambda_{max}^{MeOH}$)nm:234, 244, 254, 282, 290

The (R) compound:

Mass spectrum (me/e)=750, 688, 632, 588, 573, 486, 485, 450

UV spectrum ($\lambda_{max}^{MeOH}$)nm: 234, 241(sh), 253.5, 282, 290

EXAMPLE 1

In 20 ml of dry dichloromethane is dissolved 225.6 mg of maytansinol. To the solution are added 495 mg of DCC, 106 mg of DMAP and 420 mg of N-tert-butoxycarbonylglycine. The mixture is stirred at room temperature for about 5 minutes, whereby the reaction is completed. Then, the reaction mixture is filtered to remove the insolubles, the filtrate is concentrated under reduced pressure and the residue is purified by silica gel column chromatography to yield 204 mg of maytansinol 3-N-tert-butoxycarbonylaminoacetate.

$R_f$=0.82 (solvent=water-saturated ethyl acetate); Mass spectrum (m/e): 721(M+), 660 (M+-61), 604.

EXAMPLE 2

In 2.5 ml of dry dichloromethane is dissolved 88 mg of maytansinol 3-N-tert-butoxycarbonylaminoacetate. To the solution, under cooling with ice and stirring, 4.0 ml of 50% trifluoroacetic acid in dichloromethane is added. Then, at room temperature, the mixture is stirred for about 10 minutes to complete the reaction. To this reaction mixture are added 10 ml of chloroform and 5 ml of water and after the water layer is made alkaline with a saturated aqueous solution of sodium hydrogen carbonate, the organic layer is separated. The water layer is further extracted twice with 5 ml portions of chloroform and the organic layers are combined, washed with water and dried over anhydrous sodium sulfate. The solvent is then distilled off and the residue is purified by silica gel column chromatography to yield 105 mg of maytansinol 3-aminoacetate. $R_f$=0.5 (solvent: acetonitrile-water=9:1 , v/v); mass spectrum (m/e): 560(M+-61), 485

EXAMPLE 3

As in Example 1, 282 mg of maytansinol, 618 mg of DCC, 127 mg of DMAP and 750 mg of N-tert-butoxycarbonyl-L-phenylglycine are stirred in 20 ml of dry dichloromethane for about 30 minutes. The reaction mixture is subjected to silica gel chromatography (solvent: chloroform-methanol=100:1, v/v) as in Example 1, whereby the following two fractions are obtained in the order of emergence. Fraction I (170 mg) and Fraction II (110 mg). These products are two stereoisomers of maythansinol 3-(α-N-tert-butoxycarbonylamino)-phenylacetate with respect to the center of asymmetry in the phenylalanine moiety.

Fraction I, $R_f$=0.57; Fraction II, $R_f$0.50 (solvent: chloroform-methanol=95:5, v/v). Mass spectrum (m/e): Fraction I: 750 (M+-61), 717, 694; Fraction II: 750(M+-61), 717, 694.

EXAMPLE 4

In 2 ml of dry dichloromethane is dissolved 143 mg of maytansinol 3-N-tert-butoxycarbonylphenylalanine (Fraction I, according to Example 3), and under ice-cooling and stirring, 1 ml of a 50% solution of trifluoroacetic acid in dichloromethane is added. The mixture is stirred at room temperature for about 15 minutes, after which 10 ml of chloroform and 4 ml of water are added. The water layer is made alkaline with a saturated aqueous solution of sodium hydrogen carbonate and the organic layer is separated. The water layer is further extracted twice with 5 ml portions of chloroform and the organic layers are combined, washed with water and dried. Thereafter, the solvent is distilled off and the residue is purified by silica gel column chromatography. By the above procedure is obtained 46 mg of maytansinol 3-α-aminophenyl propionate (one of the diastereomers). $R_f$=0.48 (solvent: acetonitrile-water=95:5). Mass spectrum (m/e): 650 (M+-61), 588, 573.

Then, 81 mg of Fraction II according to Example 3 is treated with 1 ml of dichloromethane and 0.5 ml of 50% trifluoroacetic acid in dichloromethane, whereby 29 mg of maytansinol 3-α-aminophenylpropionate (one of diastereomers) is obtained. $R_f$=0.40 (solvent: acetonitrile-water=95:5). Mass spectrum (m/e/): 650(M+-61), 588, 573.

EXAMPLE 5

As in Example 1, 300 mg of maytansinol, 798 mg of N-tert-butoxycarbonyl-D-phenylglycine, 655 mg of DCC and 134.6 mg of DMAP are reacted in 20 ml of dry dichloromethane to give a mixture of two diastereoisomers of maytansinol 3-(α-N-tert-butoxycarbonylamino)phenylacetate with respect to the center of asymmetry in the phenylglycine moiety. This mixture is fractionated and purified by silica gel column chromatography using a mixture of chloroform and methanol (100:1) as solvent. Fraction I (277 mg) and Fraction II (60 mg), in the order of elution, respectively. Fraction I, $R_f$=0.81; Fraction II, $R_f$=0.72 (solvent: chloroform-methanol=95:5). Mass spectrum (m/e): Fraction I: 736(M+-61), 735, 703, 680; Fraction II; 736(M+-61), 735, 703, 680.

EXAMPLE 6

As in Example 2, 210 grams of maytansinol 3-(N-tert-butoxycarbonyl)phenylglycine ester (Fraction I according to Example 5) is treated with 2 ml of dry dichloromethane and 1.2 ml of 50% trifluoracetic acid-dichloromethane to give 81 mg of maytansinol 3-α-aminophenylacetate (one of diastereomers). $R_f$=0.48 (solvent: acetonitrile-water=95:5). Mass spectrum (m/e): 636(M+-61), 574, 485.

Similarly, 60 mg of Fraction II according to Example 5 is treated with 0.5 ml of 50% trifluoroacetic acid-dichloromethane in 2 ml of dry dichloromethane to obtain 9 mg of maytansinol 3-α-aminophenylacetate (one of diastereomers). $R_f$=0.50 (developing solvent: acetonitrile-water=95/5). Mass spectrum (m/e): 636(M+-61), 574, 485.

EXAMPLE 7

As in Example 1, 56 mg of maytansinol, 79.2 mg of monomethyl succinate ester, 144 mg of DCC and 25 mg of DMAP are reacted in dry dichloromethane and the reaction product is fractionated and purified by silica gel column chromatography to yield 37 mg of maytansinol 3-(3-methoxycarbonyl) propionate. $R_f$=0.67 (solvent=chloroform-methanol=95:5). Mass spectrum (m/e): 678 (M+), 635, 617(M+-61).

EXAMPLE 8

Maytansinol 3-(3-methoxycarbonyl)propionate (37 mg) is dissolved in a mixture of 0.2 ml acetronitrile and 0.1 ml water, and under ice-cooling and stirring, 54.6 μl of 1N-aqueous sodium hydroxide solution is added, followed by addition of 100 μl of the same solution over a period of 4 hours. After about 6 hours, 10 ml of water and 10 ml of chloroform are added to the reaction mixture, followed by addition of 300 μl of 1N-aqueous hydrochloric acid. The organic layer is separated, and the water layer is extracted twice with 5 ml portions of chloroform. The organic layers are combined, washed with 5 ml of water and dried. The solvent is distilled off under reduced pressure and the residue is fractionated and purified by silica gel chromatography to yield 22 mg of maytansinol 3-(3-carboxy)propionate. $R_f=0.18$ (solvent: chloroform-methanol=9:1).

EXAMPLE 9

Maytansinol (112.8 mg) is dissolved in a mixture of 20 ml dry dichloromethane and 5 ml dry tetrahydrofuran. To this, 247.2 mg of DCC, 48.4 mg of DMAP and 409.2 mg of N-trifluoroacetyl-L-aspartic acid-α-methyl ester are added. The mixture is stirred at room temperature overnight. The insolubles are filtered off, the filtrate is concentrated under reduced pressure and the residue separated and purified by silica gel column chromatography to give 84 mg of maytansinol 3-(3-trifluoroacetamido-3-methoxycarbonyl)propionate. $R_f=0.56$ (solvent: ethyl acetate saturated with water). Mass spectrum (m/e): 789(M+), 746, 728(M+-61), 713.

EXAMPLE 10

In 2 ml of acetonitrile is dissolved 80 mg of maytansinol 3-(3-trifluoroacetamido-3-methoxycarbonyl)propionate, and to this, under ice-cooling and stirring, 200 μl of 1N-aqueous sodium hydroxide is added over a period of about 3 hours. The mixture is further stirred for an hour, and then 5 ml of wate and 15 ml of chloroform are added. The mixture is adjusted to pH 5 with 1-N-HCl. The organic layer is separated and the water layer is extracted twice with 5 ml portions of chloroform. The organic layers are pooled and dried. The solvent is thereafter distilled off and the residue separated and purified by silica gel column chromatography to yield : 8 mg of maytansinol 3-(3-amino-3-carboxy)propionate. $R_f=0.1$ (solvent: chloroform-methanol=3:2)

EXAMPLE 11

In 5 ml of dry tetrahydrofuran is dissolved 14 mg of maytansinol 3-isonicotinate, followed by addition of 11.9 mg of methyl iodide. The mixture is reacted at room temperature with continuous stirring. After the reaction has been completed, the reaction mixture is concentrated under reduced pressure. Dry ether is added to the residue and the resultant precipitate is recovered by filtration and dried to yield 6 mg of maytansinol 3-isonicotinate iodomethylate. $R_f=0.28$ (solvent: acetonitrile-water=4:1).

EXAMPLE 12

In 10 ml of dichloromethane are dissolved 282 mg of maytansinol, 666 mg of phenyl hydrogen adipate 721 mg of DCC and 122 mg of DMAP, and the solution is stirred at room temperature for 2.5 hours. The resultant precipitate is filtered off, the filtrate concentrated to dryness and the residue fractionated and purified by silica gel column chromatography to give 239 mg of maytansinol 3-(5-phenoxycarbonyl) pentanoate. $R_f=0.62$ (solvent: chloroform-methanol=95:5). Mass spectrum (m/e): 768(M+), 707(M+-61).

EXAMPLE 13

In a mixture of 3.6 ml tetrahydrofuran and 1.8 ml water is dissolved 207 mg of the maytansinol 3-(5-phenoxycarbonyl) pentanoate obtained in Example 12, and, under stirring at room temperature, 540 μl of 1N-aqueous sodium hydroxide is added. Then, at intervals of 30 minutes, two 135 μl portions of 1N-aqueous sodium hydroxide are further added and the mixture is allowed to stand at room temperature for 30 minutes. It is then neutralized with 810 μl of 1N-hydrochloric acid and the solvent is distilled off under reduced pressure. The residue is fractionated and purified by silica gel column chromatography to yield 135 mg of maytansinol 3-(5-carboxy) pentanoate. $R_f=0.49$ (solvent: acetronitrile-water=95:5). Mass spectrum (m/e): 651(M+-61).

EXAMPLE 14

As in Example 1, 80 mg of maytansinol, 177 mg of N-benzyloxycarbonylglycine, 175 mg of DCC and 28.5 mg of DMAP are reacted in 15 ml of dry dichloromethane and the reaction product is fractionated and purified by silica gel column chromatography to yield 52 mg of maytansinol 3-(α-N-benzyloxycarbonylamino)acetate. $R_f=0.64$ (solvent: ethyl acetate saturated with water). Mass spectrum (m/e), 694(M+-61), 652, 603.

EXAMPLE 15

The compound (52 mg) prepared in Example 14 is catalytically hydrogenated in 5 ml of gracial acetic acid at room temperature under hydrogen gas streams in the presence of palladium-carbon catalyst. After the reaction has been completed, the catalyst is filtered off, the filtrate concentrated to dryness under reduced pressure and the residue fractionated and purified by silica gel column chromatography. This procedure yields 15 mg of maytansinol 3-aminoacetate. The analytical data of this product has confirmed the identity of this compound to that obtained in Example 2.

EXAMPLE 16

As in Example 1, 300 mg of maytansinol, 700 mg of DCC, 1175 mg of N-α,ε-tert-butoxycarbonyl-L-lysine and 150 mg of DMAP are reacted in dry dichloromethane and the reaction product is fractionated by silica gel column chromatography. This procedure yields two diastereomers of maytansinol 3-(2,6-bis-tert-butoxycarbonylamino)hexanote with respect to the lysine moiety, i.e. Fraction I and Fraction II in the order of elution and in the amounts of 333 mg and 102 mg, respectively. Fraction I, $R_f=0.41$; Fraction II, $R_f=0.31$ (solvent: chloroform-methanol=95:5). Mass spectrum (m/e): Fraction I, 830(M+-62), 828, 798, Fraction II, 830(M+-62), 828, 798.

EXAMPLE 17

As in Example 2, 240 mg of Fraction I according to Example 16 is reacted with 1.2 ml of 50% trifluoroacetic aciddichloromethane in 2 ml of dry dichloromethane, followed by chromatographic purification on a silica gel column. This procedure yields 46 mg of maytansinol 3-(2,6-diamino)hexanoate (one of diastereomers). Mass spectrum (m/e), 631(M+-61), 598.

Then, 80 mg of Fraction II according to Example 16 is reacted with 0.5 ml of 50% trifluoroacetic acid-methylene chloride in 1 ml of dry methylene chloride in a manner similar to that above. This procedure yields 16 mg of maytansinol 3-(2,6-diamino)hexanoate (the other diastereomer). Mass spectrum (m/e): 631(M+-61), 598.

EXAMPLE 18

As in Example 1, 83 mg of maytansinol, 267.3 mg of γ-tert-butyl N-tert-butoxycarbonyl-L-glutaminate, 181.9 mg of DCC and 39.2 mg of DMAP are reacted in 10 ml of dry methylene chloride. The reaction product is fractionated and purified by silica gel column chromatography using chloroform-methanol (200:1) as the solvent. The above procedure yields two diastereomers of maytansinol 3-(2-N-tert-butoxycarbonyl-4-tert-butoxycarbonyl)butyrate due to the glutamic acid moiety Fraction I (eluted first) 43 mg; Fraction II (eluted later) 21 mg. Fraction I, $R_f=0.81$; Fraction II, $R_f=0.74$ (solvent: chloroform-methanol=95:5). Mass spectrum (m/e): Fraction I: 788(M+-61), 732, 688; Fraction II: 788(M+-61), 732, 688.

EXAMPLE 19

As in Example 2, 35 mg of Fraction I of Example 18 is reacted with 1.3 ml of 50% trifluoroacetic acid-methylene chloride in 1 ml of dry methylene chloride and the reaction product is fractionated by silica gel column chromatography to yield 7 mg of maytansinol 3-(2-amino-4-carboxy)butyrate (one of the diastereomers). $R_f=0.12$ (solvent: acetonitrile-water 9:1).

Similarly, 15 mg of Fraction II of Example 18 is reacted with 1 ml of 50% trifluoroacetic acid-methylene chloride in 1 ml of dry methylene chloride to give 5 mg of maytansinol 3-(2-amino-4-carboxy)butyrate (the other diastereomer). $R_f=0.1$ (solvent: acetonitrile-water=9:1).

EXAMPLE 20

Maytansinol 3-(S)-α-(N-methyl-N-tert-butoxycarbonyl)aminopropionate (50.3 mg) is mixed with 0.2 ml of trifluoroacetic acid. The mixture is stirred at room temperature for 20 minutes. The reaction mixture is diluted with 5 ml of dichloromethane, followed by the addition of a saturated aqueous solution of sodium hydrogen carbonate with stirring. The organic layer is separated and the water layer is extracted with ethyl acetate. The organic layers are combined, dried (Na$_2$SO$_4$) and evaporated to give 43.3 mg of crude product. The crude product is separated and purified on a silica gel plate (Merck, Art 5642) (solvent: chloroform-methanol=6:1, v/v, developed twice). The zone $R_f=0.61-0.67$ is scraped and eluted with chloroform-methanol=9:1 (v/v). The procedure yields 5.27 mg of maytansinol 3-(S)-α-N-methylaminopropionate.

Then, the product is dissolved in 0.3 ml of chloroform followed by the addition of 0.1 ml of acetic anhydride and 0.25 ml of triethylamine. The mixture is stirred at room temperature for 1 hour. To the reaction mixture is added 0.1 ml of methanol followed by extraction with ethyl acetate. The extract is dried, and the solvent is distilled off. The residue is separated by silica gel chromatography to give maytansine.

EXAMPLE 21

As in Example 20, 39.8 mg of maytansinol 3-(R)-α-(N-methyl-N-tert-butoxycarbonyl)aminopropionate is treated with 0.4 ml of trifluoroacetic acid and 31.2 mg of crude product is subjected to chromatography. The zone $R_f=0.53-0.62$ is scraped off and eluted to give 4.85 mg of maytansinol 3-(R)-α-N-methylaminopropionate.

The product is treated with acetic anhydride, whereupon D-maytansine is obtained.

EXAMPLE 22

As in Example 1, 66.3 mg of dechloromaytansinol, 155 mg of DCC, 35 mg of DMAP and 133 mg of N-tert-butoxycarbonylglycine are reacted in 5 ml of dry dichloromethane at room temperature. Thereafter, the reaction mixture is treated as in Example 1 and separated by chromatography to give 60 mg of dechloromaytansinol 3-N-tert-butoxycarbonylaminoacetate. $R_f=0.81$ (solvent: water-saturated ethyl acetate); mass spectrum (m/e): 687(M+), 626(M+-61).

As in Example 2, 23 mg of the above product is treated with trifluoroacetic acid-dichloromethane in 1 ml of dried dichloromethane, under ice-cooling. To the reaction mixture are added chloroform and water. The mixture is made alkaline with a saturated aqueous solution of sodium hydrogen carbonate and extracted with chloroform, followed by chromatography to yield 17 mg of dechloromaytansinol-3-aminoacetate. $R_f=0.5$ (solvent: acetonitril-water=9:1, v/v); mass spectrum (m/e): 526(M+-61), 485.

EXPERIMENTAL DATE

Antitumor activity

Therapeutic tests were carried out in mice according to NCI-protocol 1,300, Cancer Chemother, Reports, Part 3, 1972, Vol. 3, No. 2, in which melanoma B-16 tumor cells had been intraperitoneally transplanted, compound (I) being administered intraperitoneally once daily for 9 consecutive days. Life span prolongations obtained are shown in Table 1 as T/C % values.

TABLE 1

| Compound | Dose (μg/kg) | Antitumor activities B-16 (T/C%) |
| --- | --- | --- |
| Maytansinol | 800 | 208 |
| 3-α-aminophenylacetate | 400 | 208 |
| (Fraction I) | 100 | 208 |

Antiprotozoal activity

Antioprotozoal activity of compound (I) was assayed with *Tetrahymena pyriformis* W as the test organism and a medium composed of 20 g tryptose-peptone (Difco Co.), 1 g yeast extract, 2 g glucose, 1000 ml distilled water, 10 ml 1 M phosphate buffer (pH 7.0) as the assay medium. The micoorganism was incubated at 28° C. for 44 to 48 hours and the growth inhibitory activity of compound (I) was assayed by the serial dilution method. The minimal inhibitory concentrations of compound (I) are shown in Table 2.

TABLE 2

| Compound | Antiprotozoal activity MIC (μg/ml) *Tetrahymena pyriformis* W |
| --- | --- |
| Maytansinol 3-α-aminophenylacetate (Fraction I) | 10–20 |

Example of Pharmaceutical Composition

Composition for Injection

| | |
|---|---|
| (1) Maytansinol 3-α-aminophenylacetate | 200 mg |
| (2) Ethanol | 10 g |
| (3) Polysorbate 80 (Tween 80) | 40 g |
| (4) Mannitol | 20 g |
| (5) Distilled water, a sufficient quantity to make | 1000 ml |

Preparation (1) is dissolved in (2). To this solution, (3) and (4) are added, followed by the addition of sterilized distilled water to make 1000 ml of the solution. Ten milliliter each of the solution is used to fill 100 amber ampoules and the air within the ampoules is replaced with nitrogen gas, then the ampoule is sealed. All the processes are conducted under sterile conditions.

What we claim is:

1. A compound of the formula:

[Chemical structure]

wherein

X is H or Cl, and

R is $C_{1-8}$ alkyl, phenyl, phenyl-$C_{1-4}$ alkyl or 5- or 6-membered azaheterocyclic group containing one to four of N, of the class consisting of pyridyl, pyrimidyl, pyrazinyl, pyridazinyl, triazinyl, piperidyl, piperazinyl, imidazolyl, pyrazolyl, triazolyl, tetrazolyl, pyrrolinyl, pyrazolinyl, imidazolinyl, pyrrolidinyl, pyrazolidinyl, imidazolidinyl and triazolidinyl, said R group having one or two substituents selected from the class consisting of carboxyl, sulfo, an amino group which is unsubstituted or mono-substituted by $C_{1-4}$ alkyl, $C_{3-4}$ alkenyl, benzyl, phenyl, $C_{1-4}$ alkylsulfonyl, benzenesulfonyl and p-toluenesulfonyl, and a quaternary ammonio group of the formula:

$$-\overset{R^2}{\underset{R^4}{N^+}}-R^3$$

wherein each of $R^2$, $R^3$ and $R^4$ is independently $C_{1-4}$ alkyl, allyl pyrazolio, pyrrolinio, triazolio, tetrazolio, piperidinio, piperazinio, pyrrolidinio, pyrrolinio, imidazolinio, imidazolidinio, pyrazolinio and pyrazolidinio group.

2. A compound according to claim 1, wherein X is Cl.

3. A compound according to claim 1, wherein the azaheterocyclic group is pyridyl, piperazinyl, imidazolinyl or tetrazolyl.

4. A compound according to claim 1, wherein the quaternary ammonio group is trimethylammonio, allyldimethylammonio, benzyldimethylammonio, pyridinio, piperazinio, imidazolio or triazolio.

5. A compound according to claim 1, wherein R is $C_{1-8}$ alkyl, phenyl-$C_{1-4}$ alkyl or pyridyl, said groups having one or two substituents selected from the group consisting of carboxyl, pyridinio, amino and $C_{1-4}$ alkylamino.

6. A compound according to claim 5, wherein R is phenyl-$C_{1-4}$ alkyl substituted by amino.

7. The compound according to claim 1, which is maytansinol 3-α-aminophenylacetate.

8. The compound according to claim 1, which is maytansinol 3-α-amino-β-phenylpropionate.

9. The compound according to claim 1, which is maytansinol 3-aminoacetate.

10. An antitumor composition which comprises as an active ingredient an amount effective to inhibit the growth of tumors of a compound of the formula:

[Chemical structure]

wherein

X is H or Cl, and

R is $C_{1-8}$ alkyl, phenyl, phenyl-$C_{1-4}$ alkyl or 5- or 6-membered azaheterocyclic group containing one to four of N, of the class consisting of pyridyl, pyrimidyl, pyrazinyl, pyridazinyl, triazinyl, piperidyl, piperazinyl, imidazolyl, pyrazolyl triazolyl, tetrazolyl, pyrrolinyl, pyrazolinyl, imidazolinyl, pyrrolidinyl, pyrazolidinyl, imidazolidinyl and triazolidinyl, said R group having one or two substituents selected from the group consisting of carboxyl, sulfo, an amino group which is substituted or mono-substituted by $C_{1-4}$ alkyl, $C_{3-4}$ alkenyl, benzyl, phenyl, $C_{1-4}$ alkylsulfonyl, benzenesulfonyl and p-toluenesulfonyl, and a quaternary ammonio group of the formula:

$$-\overset{R^2}{\underset{R^4}{N^+}}-R^3$$

wherein each of $R^2$, $R^3$ and $R^4$ is independently $C_{1-4}$ alkyl, allyl or benzyl, or the quaternary ammonio group if formed at the ring N of a pyridinio, pyrazinio, pyrimidinio, pyridazinio, imidazolio, pyrazolio, pyrrolinio, triazolio, tetrazolio, piperidinio, piperazinio, pyrrolidinio, pyrrolinio, imidazolinio, imidazolidinio, pyrazolinio and pyrazolidinio group.

11. A method of inhibiting the growth of tumor cells and prolonging the survival time of a tumor-bearing warm blooded animal, which comprises administering to said animal an amount effective to inhibit the growth of tumors of a compound of the formula:

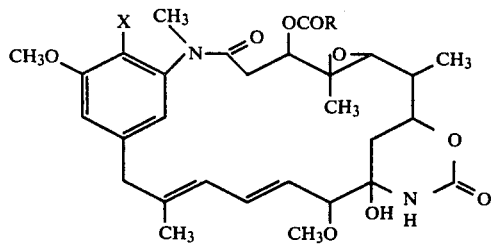

wherein

X is H or Cl, and

R is $C_{1-8}$ alkyl, phenyl, phenyl-$C_{1-4}$ alkyl or 5- or 6-membered azaheterocyclic group containing one to four of N, of the class consisting of pyridyl, pyrimidyl, pyrazinyl, pyridazinyl, triazinyl, piperidyl, piperazinyl, imidazolyl, pyrazolyl, triazolyl, tetrazolyl, pyrrolinyl, pyrazolinyl, imidazolinyl, pyrrolidinyl, pyrazolidinyl, imidazolidinyl and triazolidinyl, said R group having one or two substituents selected from the class consisting of carboxyl, sulfo, an amino group which is unsubstituted or mono-substituted by $C_{1-4}$ alkyl, $C_{3-4}$ alkenyl, benzyl, phenyl, $C_{1-4}$ alkylsulfonyl, benzenesulfonyl and p-toluenesulfonyl, and a quaternary ammonio group of the formula:

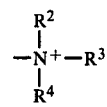

wherein each of $R^2$, $R^3$ and $R^4$ is independently $C_{1-4}$ alkyl, allyl or benzyl, or the quaternary ammonio group is formed at the ring N or a pyridinio, pyrazinio, pyrimidinio, pyridazinio, imidazolio, pyrazolio, pyrrolinio, trazolio, tetrazolio, piperidinio, piperazinio, pyrrolidinio, pyrrolinio, imidazolinio, imidazolidinio, pyrazolinio and pyrazolidinio group.

* * * * *